(12) United States Patent  (10) Patent No.: US 8,617,244 B2
Reichen et al.  (45) Date of Patent: Dec. 31, 2013

(54) INTERVERTEBRAL IMPLANT (75) Inventors: Marc Reichen, West Chester, PA (US);
Thomas Kueenzi, Downingtown, PA (US); Edwin Chan, Downingtown, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 568 days.

(21) Appl. No.: 12/817,550

(22) Filed: Jun. 17, 2010

(65) Prior Publication Data

US 2010/0324683 A1 Dec. 23, 2010

Related U.S. Application Data

(60) Provisional application No. 61/187,997, filed on Jun. 17, 2009.

(51) Int. Cl.
*A61F 2/44* (2006.01)
(52) U.S. Cl.
USPC ..................... 623/17.16; 623/17.11
(58) Field of Classification Search
USPC .......................................... 623/17.11, 17.16
See application file for complete search history.

(56) References Cited

U.S. PATENT DOCUMENTS

| 5,709,683 | A | 1/1998 | Bagby | |
|---|---|---|---|---|
| 6,743,256 | B2 | 6/2004 | Mason | |
| 7,056,341 | B2 | 6/2006 | Crozet | |
| 7,475,548 | B2 | 1/2009 | Toffan et al. | |
| 7,837,732 | B2 | 11/2010 | Zucherman et al. | |
| 2003/0233147 | A1* | 12/2003 | Nicholson et al. | 623/17.16 |
| 2005/0149193 | A1* | 7/2005 | Zucherman et al. | 623/17.11 |
| 2005/0165487 | A1 | 7/2005 | Muhanna et al. | |
| 2007/0112429 | A1 | 5/2007 | Muhanna et al. | |
| 2007/0162134 | A1* | 7/2007 | Marnay et al. | 623/17.11 |
| 2010/0042220 | A1* | 2/2010 | Tauber | 623/17.16 |

FOREIGN PATENT DOCUMENTS

| KR | 2008 0093846 A | 10/2008 |
|---|---|---|
| WO | WO 2007/098288 | 8/2007 |
| WO | WO 2008/092192 A1 | 8/2008 |

\* cited by examiner

*Primary Examiner* — Andrew Yang
*Assistant Examiner* — Olivia C Chang
(74) *Attorney, Agent, or Firm* — Woodcock Washburn LLP (57) ABSTRACT

An intervertebral implant that is configured to be inserted into an intervertebral space along a direction of insertion is provided. The intervertebral space is defined by a superior vertebral body and an inferior vertebral body that are opposed in a transverse direction. The intervertebral implant may include a body and a first keel. The body may have first and second opposing outer surfaces that are each configured to engage one of the superior and inferior vertebral bodies. The first keel may extend out from the first outer surface in an outward direction and may define a lateral width that increases with respect to an outward direction along the first keel such that an outer portion of the first keel is wider than an inner portion of the first keel. The lateral width may be substantially transverse to the insertion direction and the outward direction.

25 Claims, 11 Drawing Sheets

INTERVERTEBRAL IMPLANT

CROSS REFERENCE TO RELATED APPLICATIONS

This application claims priority to U.S. Provisional Application No. 61/187,997, filed Jun. 17, 2009, the contents of which are incorporated by reference in their entirety.

BACKGROUND

Removal of an intervertebral disc is often desired if and when the disc degenerates. The disc may be replaced with a device such as a cage or other spacer that restores the height of the disc space and allows bone growth through the device to fuse the adjacent vertebrae. Spacers often do not intimately connect the two vertebral bodies and a combination of plates and screws are often used to obtain the rigidity necessary to enable bone to grow and fuse the adjacent vertebral bodies.

Implants for spinal fusion that are impacted into the disc space and allow growth of bone from adjacent vertebral bodies through the upper and lower surfaces of the implant are known in the art. Such implants are typically provided with a lordotic taper to enable a surgeon to recreate an appropriate lordotic curvature to the motion segment. In order to create the appropriate environment for fusion, fixation hardware is applied to the spinal segment to limit the relative motion between the vertebral bodies to be fused.

Furthermore, interbody implants that feature a screw thread form connected to a central body have been developed, such as the well-known cylindrical threaded spacers. These devices are typically hollow and allow bone growth through fenestrations in the device. Clinically, these devices are associated with the risk of post-operative loss of disc height due to the small surface area available to resist subsidence into the adjacent vertebral body relative to design of the impacted cages.

Attempts to combine the features of the impacted implants with the implants using screw thread forms, provide a greater resistance to subsidence; however, they offer little resistance to anatomic motions where the vertebral bodies move apart from each other, such as is typical in flexion and lateral bending.

SUMMARY

An intervertebral implant that is configured to be inserted into an intervertebral space along a direction of insertion is provided. The intervertebral space is defined by a superior vertebral body and an inferior vertebral body that are opposed in a transverse direction. The intervertebral implant may include a body and a first keel. The body may have first and second opposing outer surfaces that are each configured to engage one of the superior and inferior vertebral bodies. The first keel may extend out from the first outer surface in an outward direction and may define a lateral width that increases with respect to an outward direction along the first keel such that an outer portion of the first keel is wider than an inner portion of the first keel. The lateral width may be substantially transverse to the insertion direction and the outward direction.

In another embodiment the intervertebral implant may include a body and a first keel. The body may have first and second opposing outer surfaces, that are each configured to engage one of the inferior and superior vertebral bodies, a posterior side, and an opposing anterior side. The first keel may extend out from the first outer surface and may define a first inner surface that faces the first outer surface of the body. A distance between the first inner surface and the first outer surface of the body may increases along the direction of insertion.

A method of implanting an intervertebral implant into an intervertebral space along a direction of insertion is also provided. The intervertebral space is defined by a superior vertebral body and an inferior vertebral body that are opposed in a transverse direction. In such a method a first keel cut may be formed into the superior vertebral body and a second keel cut may formed into the inferior vertebral body. The first keel cut may have a first portion and a second portion extending up from the first portion along the transverse direction. The first and second portions may define a width that extends substantially perpendicular to both the transverse direction and the direction of insertion. The width of the second portion is greater than the width of the first portion. The second keel cut may have a first portion and a second portion extending down from the first portion along the transverse direction. The first and second portions may define a width that extends substantially perpendicular to both the transverse direction and the direction of insertion. The width of the second portion is greater than the width of the first portion. The intervertebral implant may then be inserted into the intervertebral space. The intervertebral implant may have a body, a first keel extending up from a superior surface of the body, and a second keel extending down from an inferior surface of the body. The first and second keels each include a locking member that is configured to be received by a respective second portion of the first and second keel cuts formed in the superior and inferior vertebral bodies.

BRIEF DESCRIPTION OF THE DRAWINGS

The foregoing summary, as well as the following detailed description of an example embodiment of the application, will be better understood when read in conjunction with the appended drawings, in which there is shown in the drawings an example embodiment for the purposes of illustration. It should be understood, however, that the application is not limited to the precise arrangements and instrumentalities shown. In the drawings.

DETAILED DESCRIPTION OF ILLUSTRATIVE EMBODIMENTS

Figure 1:
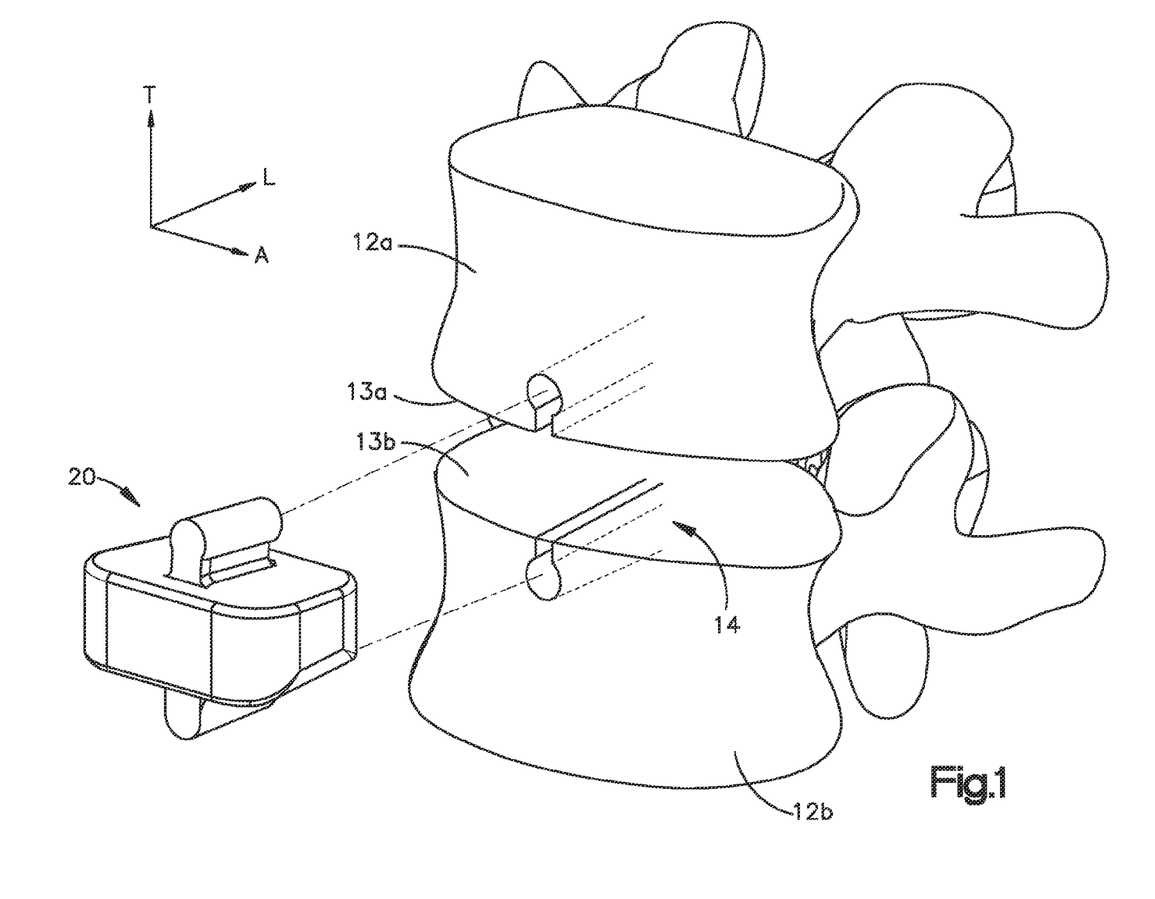
FIG. 1 is a perspective view of an interbody implant being inserted into a pair of vertebral bodies separated by an intervertebral space.

Referring to FIG. 1, a superior vertebral body 12a defines an inferior vertebral endplate of an intervertebral disc space 14, and an adjacent inferior vertebral body 12b defines a superior vertebral endplate 13b, such that the intervertebral disc space 14 is disposed and defined between the endplates 13a-b. Thus, the intervertebral disc space 14 is disposed between the vertebral bodies 12a-b. In this regard, it should be appreciated that the inferior vertebral endplate 13a provides a superior surface of the intervertebral space 14, and the superior vertebral endplate 13b provides an inferior surface of the intervertebral disc space 14. The vertebral bodies 12a-b can be anatomically adjacent vertebral bodies, or can remain after a corpectomy has been performed that removed a vertebral body from a location between the vertebral bodies 12a-b. As illustrated, the intervertebral disc space 14 is illustrated after a discectomy has been performed, whereby the disc material has been removed or at least partially removed from the intervertebral disc space 14 to prepare the intervertebral disc space 14 to receive an implant, such as implant 20, shown in FIGS. 2A-2F. When implanted in the intervertebral disc space 14, the implant 20 can restore height to the intervertebral disc space 14. The intervertebral space 14 can be disposed anywhere along the spine as desired, for instance in the lumbar region, the thoracic region, or the cervical region.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The implant 20 may be an interbody spacer implant and is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the interbody spacer implant 20 is implanted into an intervertebral space, such as the intervertebral space 14, the transverse direction T extends generally along the superior-inferior (or caudal-cranial) direction, while the plane defined by the longitudinal direction L and lateral direction A lie generally in the anatomical plane defined by the anterior-posterior direction, and the medial-lateral direction. Accordingly, the directional terms "vertical" and "horizontal" are used to describe the interbody spacer implant 20 and its components as illustrated merely for the purposes of clarity and illustration.

Referring now also to FIGS. 2A-2D, an interbody spacer implant 20 is configured to be positioned within an at least partially cleared out disc space, such as the disc space 14. The interbody spacer implant 20 can be formed entirely from allograft bone, however, at least a portion of the entirety of the implant 20 may be formed from a range of alternate biocompatible materials or combinations of materials, including polymers, such as PEEK, porous PEEK, carbon fiber-reinforced PEEK, titanium and titanium alloys, stainless steel, ceramic, polylactic acid, tantalum, and magnesium. It should be understood that no portion of the implant 20 must be formed from allograft bone, and that a portion or all of the implant 20 may be made from the alternative materials.

Figure 2A:
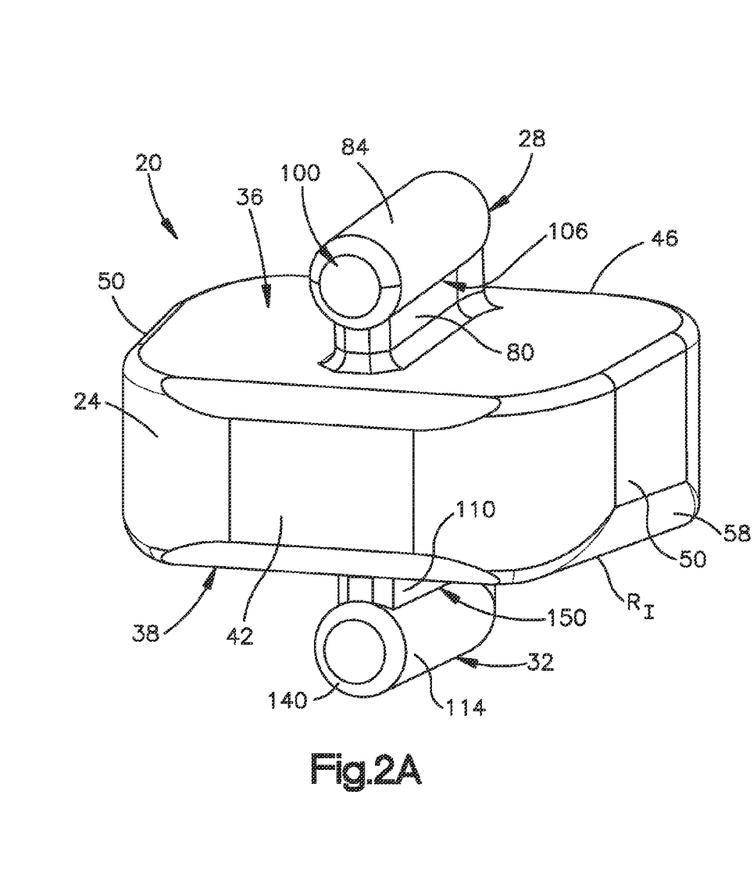
FIG. 2A is a perspective view of an interbody spacer implant having a body, a first keel, and a second keel, in accordance with one embodiment.

The implant 20 includes a body 24 that defines an upper or superior, or outer, engagement surface 36 configured to contact the inferior endplate 13a of the superior vertebral body 12a, and a lower or inferior, or outer engagement surface 38 configured to contact the superior endplate 13b of the inferior vertebral body 12b. The body 24 further defines a posterior side 42, an anterior side 46, and opposing lateral sides 50 that join the posterior side 42 and the anterior side 46. The posterior side 42 defines a leading edge with respect to implant insertion into the disc space 14, while the anterior side 46 defines a trailing edge with respect to implant insertion into the disc space 14. Thus, a first longitudinal direction refers to a longitudinal direction from the anterior side 46 toward the posterior side 42, and a second longitudinally direction refers to a longitudinal direction from the posterior side 42 toward the anterior side 46. The first longitudinal direction can also be referred to as a direction of implant insertion into the disc space 14 and the second longitudinal direction can also be referred to as a direction opposite the implant insertion direction, though it should be appreciated that the insertion direction need not be purely longitudinal. As shown, the body 24 and in particular the superior surface 36, the inferior surface 38, the posterior side 42, the anterior side 46, and the later sides 50 define a trapezoid and are shaped to correspond to an intervertebral space, such as the intervertebral space 14 shown in FIG. 1.

Figure 2B:
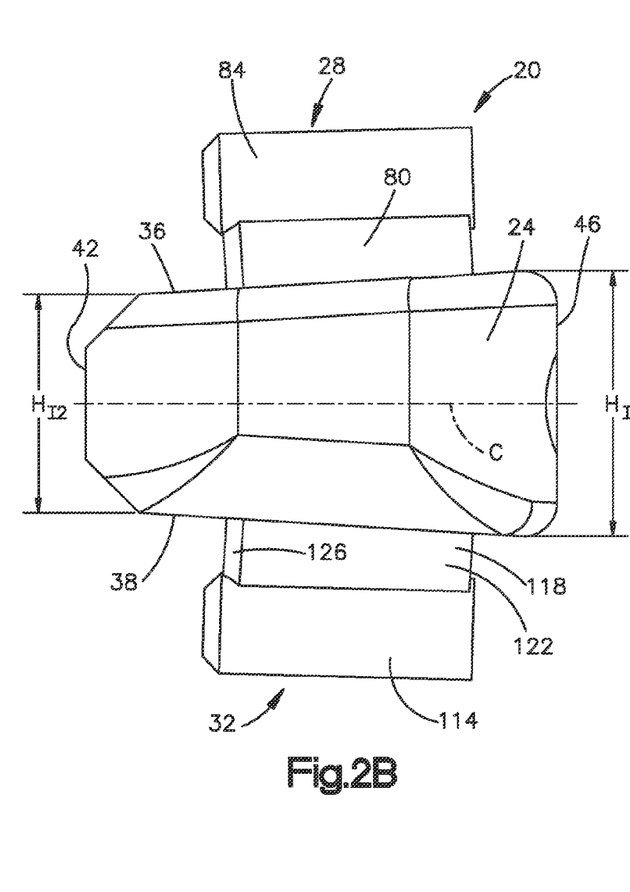
FIG. 2B is a side elevation view of the interbody spacer implant illustrated in FIG. 2A.
Figure 2C:
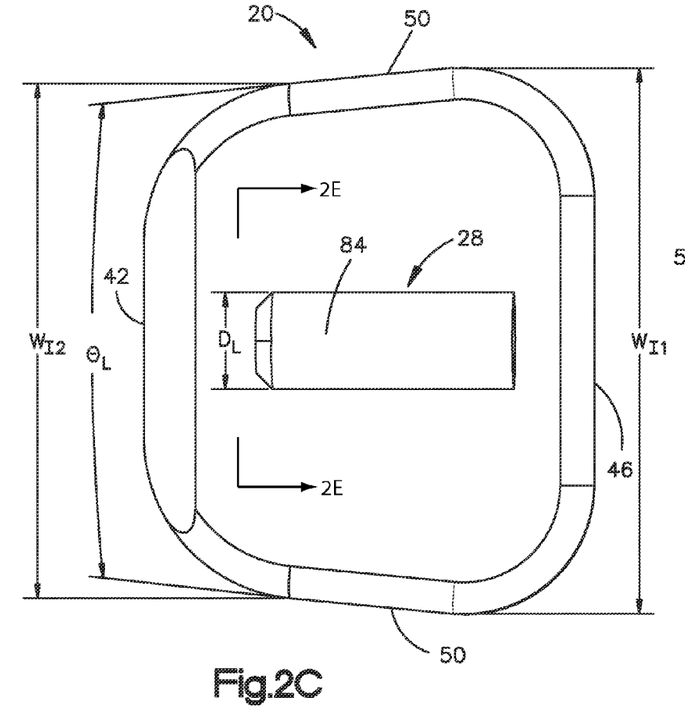
FIG. 2C is a top plan view of the interbody spacer implant illustrated in FIG. 2A.
Figure 2D:
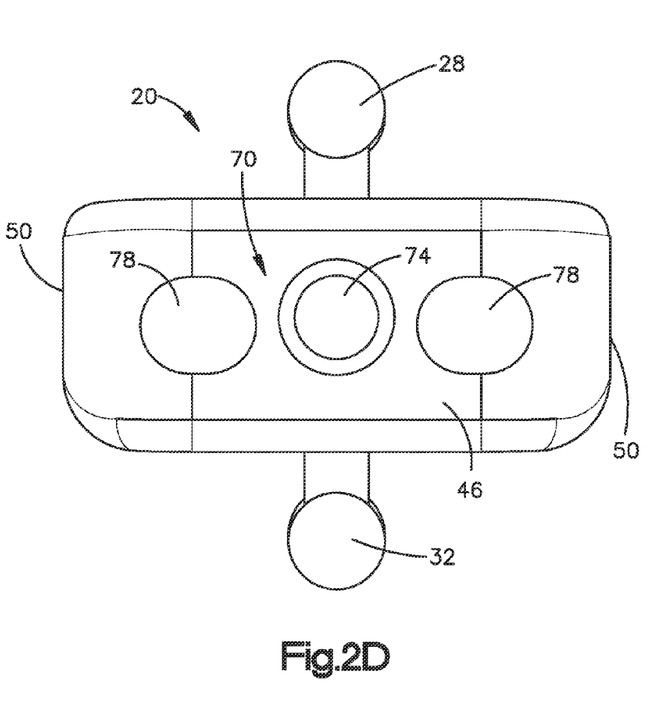
FIG. 2D is a back view of the interbody spacer implant illustrated in FIG. 2A.
Figure 2E:
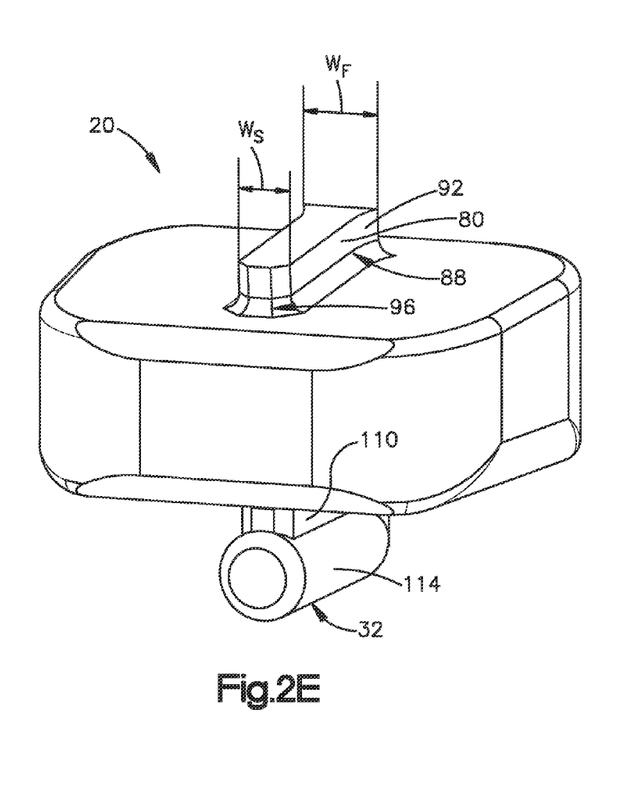
FIG. 2E is a cross-sectional view through the line 2E-2E of the interbody spacer implant illustrated in FIG. 2C.
Figure 2F:
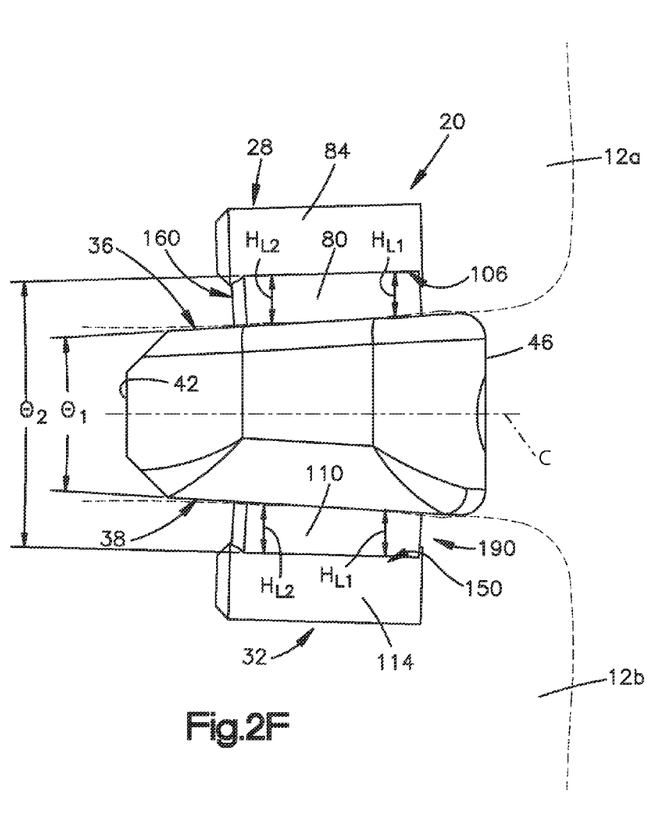
FIG. 2F is a side elevation view of the interbody spacer implant illustrated in FIG. 2A showing an angular relationship between the first and second keels and of outer surfaces of the implant body.

In that regard, and in reference to FIGS. 2B and 2F, the anterior side 46 of the implant body 24 has a first height $H_{T1}$ and the posterior side 42 of the implant body 24 has a second height $H_{T2}$. As shown, the first height $H_{T1}$ is greater than the second height $H_{T2}$. Because of the difference in heights, the superior surface 36 and the inferior surface 38 converge toward each other along the first longitudinal direction. It can also be said that the superior surface 36 and the inferior surface 38 converge toward a central longitudinal axis C of the implant body 24. As shown in FIG. 2F, the superior surface 36 and the inferior surface 38 converge toward each other at a first angle $Ø_1$ with respect to each other. The first angle $Ø_1$ may be chosen so that the implant 20 corresponds to a lordotic angle. However, it should be understood that first angle $Ø_1$ may be any desired angle. Furthermore, while the illustrative embodiment shows the superior surface 36 and the inferior surface 38 of the implant body 24 extending linearly, it should be understood that that the surfaces 36, 38 may include undulations or other non-linear portions, while still generally converging toward each other.

As shown in FIG. 2C, the sides 50 of the implant body 24 also converge toward each other. In that regard, the anterior side 46 of the implant body 24 has a first width $W_{f1}$ and the posterior side 42 of the implant body 24 has a second width $W_{f2}$. As shown, the first width $W_{f1}$ is greater than the second width $W_{f2}$. Because of the difference in widths, the surfaces of the lateral sides 50 converge toward each other along the first longitudinal direction at an angle $\varnothing_L$.

Referring to FIG. 2A, each lateral side 50 includes an inferior edge 58 that is rounded and extends along the entire longitudinal length of the lateral sides 46. As shown, the rounded edges 58 are each defined by a radius $R_I$ that can be dimensioned as desired. In accordance with the illustrated embodiment, the radius $R_I$ substantially conforms to the radius of curvature of the uncinate processes of the superior endplate 13b of the inferior vertebra 12b. Because the radius $R_I$ corresponds to the radius of curvature of the uncinate processes, the implant 20 may be more easily received within the intervertebral space.

The posterior side 42 of the implant body 24 can be shaped as desired, and is beveled or bullet shaped in accordance with the illustrated embodiment. The beveled posterior side 42 allows distraction of the vertebral bodies 12a and 12b during insertion of the implant 20. Therefore, the beveled shape may allow the implant 20 to be more easily received within the intervertebral space.

As shown in FIG. 2D, the anterior side 46 of the implant body 24 defines an engagement member 70 configured to mate with a complementary engagement member of an insertion instrument so as to couple to the implant 20 with the insertion instrument to thereby facilitate insertion of the implant 20 into the intervertebral space 14. As shown, the engagement member 70 includes a central bore 74 that extends into the body 24, and a side bore 78 extending into the body 24 on either side of the central bore 74. The central bore 74 includes internal threads that are configured to engage external threads of the insertion instrument to thereby couple the implant 20 to the insertion instrument. The side bores 78 are configured to receive protrusions of the insertion instrument to prevent or limit rotation of the implant 20 during insertion of the implant 20 into the intervertebral space.

As shown in FIGS. 2A-2F, the implant 20 further includes a first keel 28 that extends up (or transversely out) from the body 24, and a second keel 32 that extends down (or transversely out) from the body 24. In accordance with the illustrated embodiment, the first keel 28 extends out from the superior engagement surface 36, and the second keel 32 extends out from the inferior engagement surface 38. The first keel 28 and the second keel 32 are configured to engage respective keel cuts formed in the superior and inferior vertebral bodies 12a and 12b. Generally the first keel 28 and the second keel 32 extend out from the body 24 in a direction that is substantially perpendicular to the superior surface 36 and the inferior surface 38 of the implant body 24, respectively, though it should be understood that the first and second keels 28, 32 are not limited to extending perpendicular from their respective surfaces 36 and 38. For instance, the first keel 28 may extend up or transversely out from the superior surface 36 at any desired angle, and similarly, the second keel 32 may extend down or transversely out from the inferior surface 38 at any angle, so long as the first and second keels 28, 32 extend in a direction that has at least a vertical directional component that is transverse to the inferior and superior surfaces 36, 38.

As best shown in FIGS. 2A and 2E, the first keel 28 includes a first support 80 and a first locking member 84 disposed at an outer end of the first support 80. As shown in FIG. 2E, the first support 80 is a pedestal that extends up from the superior surface 36 of the implant body 24 along a central axis of the implant body 24. The first support 80 is elongate in the longitudinal direction L between the anterior side 46 and the posterior side 42 of the implant body 24. Generally, the first support 80 has a lateral width $W_S$. The lateral width $W_S$ may be at least approximately 2 mm, though it should be understood that any lateral width $W_S$ may be suitable.

As best shown in FIG. 2E, the first support 80 defines an anterior portion 88 and a posterior portion 96 that is opposed from the anterior portion 88 along the longitudinal direction. The anterior portion 88 of the first support 80 defines a flare 92 and the posterior portion 96 of the first support 80 is tapered. The flare 92 curves out with respect to a longitudinally central axis of the first support 80 in the lateral direction A along the longitudinally rearward direction. In other words, a lateral width of the anterior portion 88 of the first support 80 increases along the second longitudinal direction toward the anterior side 46 of the implant body 24, to thereby define the flare 92. Generally, the widest portion of the flare 92 has a lateral width $W_F$ that may be at least approximately 3 mm, though it should be understood that any lateral width $W_F$ may be suitable so long as it is wider than the general lateral width $W_S$ of the first support 80. The flare 92 may help the implant 20 resist anterior migration after the implant 20 has been inserted into the intervertebral space. For example, the flare 92 may catch the cortical wall of the vertebra after the implant 20 has been inserted to thereby prevent the implant 20 from migrating out of the intervertebral space. Also shown in FIG. 2E, the posterior portion 96 of the first support 80 is curved or tapered inwardly along the first longitudinal direction so as to allow the implant 20 to more easily be inserted into the intervertebral space.

Referring to FIGS. 2A and 2C, the first locking member 84 extends transversely out from the first support 80, or is otherwise disposed at a transverse outer end of the first support 80. As shown in FIG. 2A, the first locking member 84 defines a cylinder that extends along a longitudinal central axis, and is elongate in the longitudinal direction L between the anterior side 46 and the posterior side 42 of the implant body 24. As shown in FIG. 2C, the locking member 84 may have a lateral width or diameter $D_L$ that is greater than the lateral width $W_S$ of the first support 80. In this regard, it can be said that the lateral width of the first keel 28 increases with respect to an transversely outward direction along the first keel 28 such that an outer transverse portion of the first keel 28 is wider than an inner transverse portion of the first keel 28. The lateral width or diameter $D_L$ of the locking member 84 may be at least approximately 3 mm, though it should be understood that any diameter $D_L$ may be suitable. Like the first support 80, a posterior portion 100 of the first locking member 84 is curved or otherwise tapered. The tapered posterior portion 100 allows the implant 20 to more easily be inserted into the intervertebral space.

As best shown in FIGS. 2A and 2F, the locking member 84 includes an inner or body facing surface 106 that faces the superior surface 36 of the implant body 24. The body facing surface 106 may directly face the superior surface 36 of the implant body 24, or face in a direction that has at least some vertical or transverse directional component that extends toward the superior surface 36 of the implant body 24.

Referring to FIG. 2A, the second keel 32 is constructed as described above with respect to the first keel 28, and includes a second support 110 and a second locking member 114 disposed at an outer end of the second support 110. As shown, the second support 110 is a pedestal that extends down or transversely out from the inferior surface 38 of the implant body 24 along a central axis of the implant body 24. The second support 110 is elongate in the longitudinal direction L between the anterior side 46 and the posterior side 42 of the implant body 24. Generally, the second support 110 is similar to the first support 80 and has a lateral width $W_S$. Thus, the lateral width $W_S$ of the second support 110 may also be at least approximately 2 mm, though it should be understood that any lateral width $W_S$ may be suitable.

As with the first support 80 and in reference to FIGS. 2B and 2E, an anterior portion 118 of the second support 110 defines a flare 122 and a posterior portion 126 of the second support 110 is tapered. The flare 122 curves out from a longitudinal central axis of the second support 110 in the lateral direction A. In other words, a lateral width of the anterior portion 118 of the second support 110 increases as the second support 110 extends toward the anterior side 46 of the implant body 24 to thereby define the flare 122. Generally the widest portion of the flare 122 has a lateral width $W_F$ that may be at least approximately 3 mm, though it should be understood that any lateral width $W_F$ may be suitable so long as it is wider than the lateral width $W_S$ of the second support 110. The flare 122 may help the implant 20 resist anterior migration, after the implant 20 has been inserted into the intervertebral space. For example, the flare 122 may catch the cortical wall of the inferior vertebra after the implant 20 has been inserted to thereby prevent the implant 20 from migrating out of the intervertebral space. Also shown in FIG. 2E, a posterior portion 126 of the second support 110 is curved or tapered to allow the implant 20 to more easily be inserted into the intervertebral space.

As best shown in FIGS. 2A and 2B, the second locking member 114 extends out from the second support 110, or is otherwise disposed at an outer end of the second support 110. As shown in FIG. 2A, the second locking member 114 defines a cylinder that is elongate in the longitudinal direction L between the anterior side 46 and the posterior side 42 of the implant body 24. As with the first locking member 84, the second locking member 114 may have a lateral width or diameter $D_L$ that is wider than the lateral width $W_S$ of the second support 110. In this regard, it can be said that the lateral width of the second keel 32 increases with respect to an outward direction along the second keel 32 such that an outer portion of the second keel 32 is wider than an inner portion of the second keel 32. The lateral width or diameter $D_L$ of the locking member 114 may be at least approximately 3 mm, though it should be understood that any diameter $D_L$ may be suitable. Like the second support 110, a posterior portion 140 of the second locking member 114 is curved or otherwise tapered. The tapered posterior portion 140 allows the implant 20 to more easily be inserted into the intervertebral space.

As best shown in FIG. 2A, the locking member 114 includes an inner or body facing surface 150 that faces the inferior surface 38 of the implant body 24. The body facing surface 150 may directly face the inferior surface 38 of the implant body 24, or face in a direction that has at least some vertical component that extends toward the inferior surface 38 of the implant body 24.

Referring to FIG. 2F, the first locking member 84 and the second locking member 114 or at least the body facing surface 106 of the first locking member 84 and the body facing surface 150 of the second locking member 114 converge toward each other along the first longitudinal direction. It can also be said that the first locking member 84 and the second locking member 114, or at least body facing surface 106 and the body facing surface 150 converge toward the central longitudinal axis C of the implant body 24 along the first longitudinal direction L. In accordance with the illustrated embodiment, the first and second locking members 84, 114 or at least their respective body facing surfaces 106 and 150 converge toward each other at a second angle $\varnothing_2$ with respect to each other along the first longitudinal direction. The second angle $\varnothing_2$ is less than the first angle $\varnothing_1$ that is defined between the superior and inferior surfaces 36, 38 of the implant body 24. The second angle $\varnothing_2$ may be any desired angle, though it is preferred that the second angle $\varnothing_2$ is less than the first angle $\varnothing_1$. Thus, at least one or both of the body facing surfaces 106 and 150 diverge from the superior surface 36 and the inferior surface 38, respectively, along the first longitudinal direction. Otherwise stated, at least one or both of the body facing surfaces 106 and 150 converge toward the superior surface 36 and the inferior surface 38, respectively, along the second longitudinal direction. While the illustrative embodiment shows the body facing surface 106 and the body facing surface 150 extending linearly, it should be understood that that the surfaces 106, 150 may include undulations or other non-linear portions, while still generally converging toward each other.

As shown in FIG. 2F, a first gap 160 is defined between the body facing surface 106 of the first locking member 84 and the superior surface 36 of the implant body 24. Because of the difference between the first and second angles $\varnothing_1$, $\varnothing_2$, the height of the gap 160 decreases along the second longitudinal direction from the posterior end 42 to the anterior end 46 of the body 24. Thus, an anterior portion of the body facing surface 106 is separated from the superior surface 36 by a first distance $H_{L1}$, and a posterior portion of the body facing surface 106 is separated from the superior surface 36 by a second distance $H_{L2}$ that is greater than the first distance $H_{L1}$.

Similarly, a second gap 190 is defined between the body facing surface 150 of the second locking member 114 and the inferior surface 38 of the implant body 24. As with the first gap 160, the height of the second gap 190 decreases along the longitudinal direction from the posterior end 42 to the anterior end 46 of the body 24. Thus, an anterior portion of the body facing surface 150 is also separated from the inferior surface 38 by a first distance $H_{L1}$, and a posterior portion of the body facing surface 150 is separated from the inferior surface 38 by a second distance $H_{L2}$ that is greater than the first distance $H_{L1}$. It should be understood that while the illustrated embodiment shows the first gap 160 and the second gap 190 being substantially similar, the two gaps may have different heights.

The gaps 160 and 190 are configured to receive bone as the implant 20 is inserted into the intervertebral space. Because the gap 160 has a height that decreases along the second longitudinal direction, the surfaces 106 and 36 are configured to compress bone, such as a portion of the superior vertebral body 12a that is received in the gap 160 as the implant 20 is implanted along the insertion direction. Likewise, because the gap 190 has a height that decreases along the second longitudinal direction, the surfaces 150 and 38 are configured to compress bone, such as a portion of the inferior vertebral body 12b that is received in the gap 160 as the implant 20 is implanted along the insertion direction. The bone compression can stimulate bone growth, and cause the bone to flow around the first and second keels 28, 32 according to Wolff's Law.

Figure 3A:
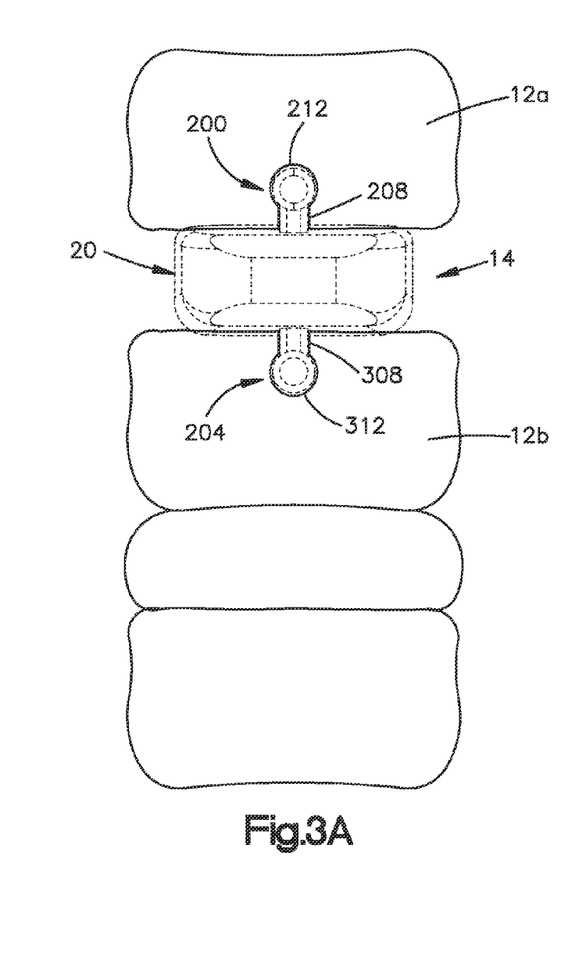
FIG. 3A is a front view of the pair of vertebral bodies illustrated in FIG. 1 with keel cuts configured to receive the interbody spacer implant therebetween.
Figure 3B:
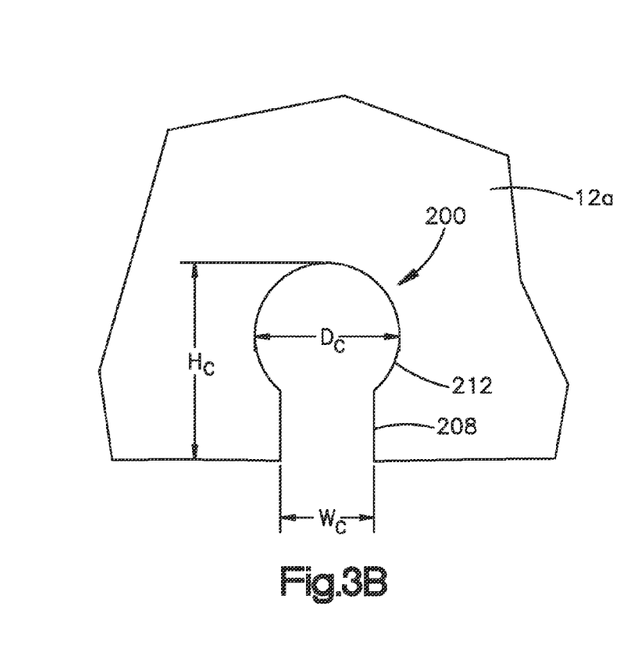
FIG. 3B is an enlarged front view of a first keel cut of the vertebral bodies illustrated in FIG. 3A.

Referring now to FIGS. 3A and 3B, a first keel cut 200 may be formed in the superior vertebral body 12a and a second keel cut 204 may be formed in the inferior vertebral body 12b. The first and second keel cuts 200, 204 are each configured to receive the first and second keels 28 and 32, respectively, of the implant 20.

The first keel cut 200 includes a lower or inner transverse first portion 208 and an upper or outer transverse second portion 212, and defines an overall height of $H_C$. The height $H_C$ of the first keel cut 200 preferably is the same height as the first keel 28 and may be approximately 4 mm, though any height $H_C$ may be desired. The first portion 208 is generally slot shaped and extends into the superior vertebral body 12a. The first portion 208 has a lateral width $W_C$ that is substantially equal to the lateral width $W_S$ of the first support 80 of the first keel 28. The second portion 212 is generally cylindrically shaped and extends up from the first portion 208. The second portion 212 has a lateral width or diameter $D_C$ that is at least substantially equal to the diameter $D_S$ of the first locking member 84 of the first keel 28. The diameter $D_S$ can be greater than the diameter $D_C$ as illustrated. Because the locking member 84 is larger than the second portion 212 of the first keel cut 200, the bone will be further compressed as the implant 20 is inserted into the intervertebral space 14.

The second keel cut 204 can be constructed as described above with respect to the first keel cut 200, and includes an upper or inner transverse first portion 308, and a lower or outer transverse second portion 312, and has an overall height of $H_C$. The height $H_C$ of the second keel cut 204 preferably is the same height as the second keel 32 and may be approximately 4 mm, though any height $H_C$ may be desired. The first portion 308 is generally slot shaped and extends into the inferior vertebral body 12b. The first portion 308 has a lateral width $W_C$ that is substantially equal to the lateral width $W_S$ of the second support 110 of the second keel 32. The second portion 312 is generally cylindrically shaped and extends down from the first portion 308. The second portion 312 has a lateral width or diameter $D_C$ that is at least substantially equal to the diameter $D_S$ of the second locking member 114 of the second keel 32. Though not required it is preferable that $D_S$ is greater than $D_C$. Because the locking member 114 is larger than the second portion 312 of the second keel cut 204, the bone will be further compressed as the implant 20 is inserted into the intervertebral space.

The first and second keel cuts 200, 204 or at least portions of the first and second keel cuts 200, 204, may be formed in the superior and inferior vertebral bodies 12a, 12b using certain instruments and methods described in US Publication No. 200100076443, filed Jul. 30, 2007 and titled "Drilling/Milling Guide and Keel Cut Preparation System," the contents of which are incorporated herein by reference in their entirety. FIGS. 4A-4E illustrate example instruments that may be used to prepare the intervertebral space 14, and in particular the keel cuts 200, 204 prior to insertion of the implant 20. Though it should be understood, however, that the first and second keel cuts 200, 204, or at least portions of the first and second keel cuts 200, 204 may be formed using any instruments and methods.

Figure 4A:
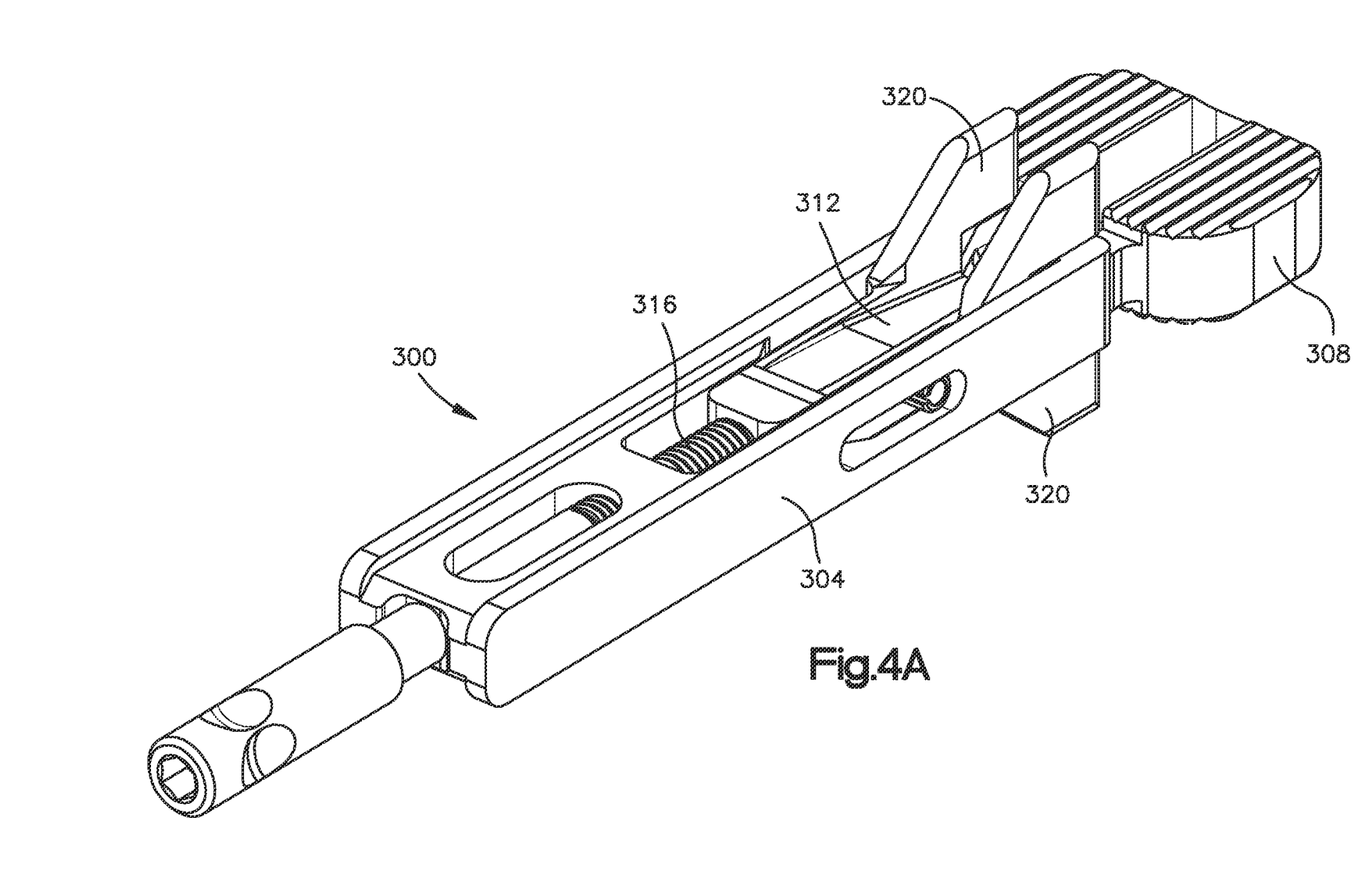
FIG. 4A is a perspective view of a trial implant including a trial implant body and a trial implant head in accordance with a first embodiment.

In reference to FIG. 4A, a trial implant 300 is used to determine the correct height of the implant 20 to be used. As shown, the trial implant 300 includes a body 304 and a distal trial head 308 that is to be inserted into the intervertebral space 14. The trial implant 300 further includes a longitudinally adjustable stop 312 that is movably mounted to the body 304 by a threaded shaft 316. The adjustable stop 312 includes upper and lower vertebra engaging members 320 whose longitudinal position relative to the trial head 308 is thus adjustable. The engaging members 320 are attached to the shaft 316 and guided for movement in the trial body 304. The engaging members 320 are positioned symmetrically relative to the midline of the trial implant 300 for an improved resistance to certain forces. In addition, the split design of the engaging members 320 allows a reamer to move in between the two engaging members 320, with the engaging members 320 offering additional soft tissue protection from the reamer. The body 304 serves as a base for a milling guide to be connected to be mounted on.

Figure 4B:
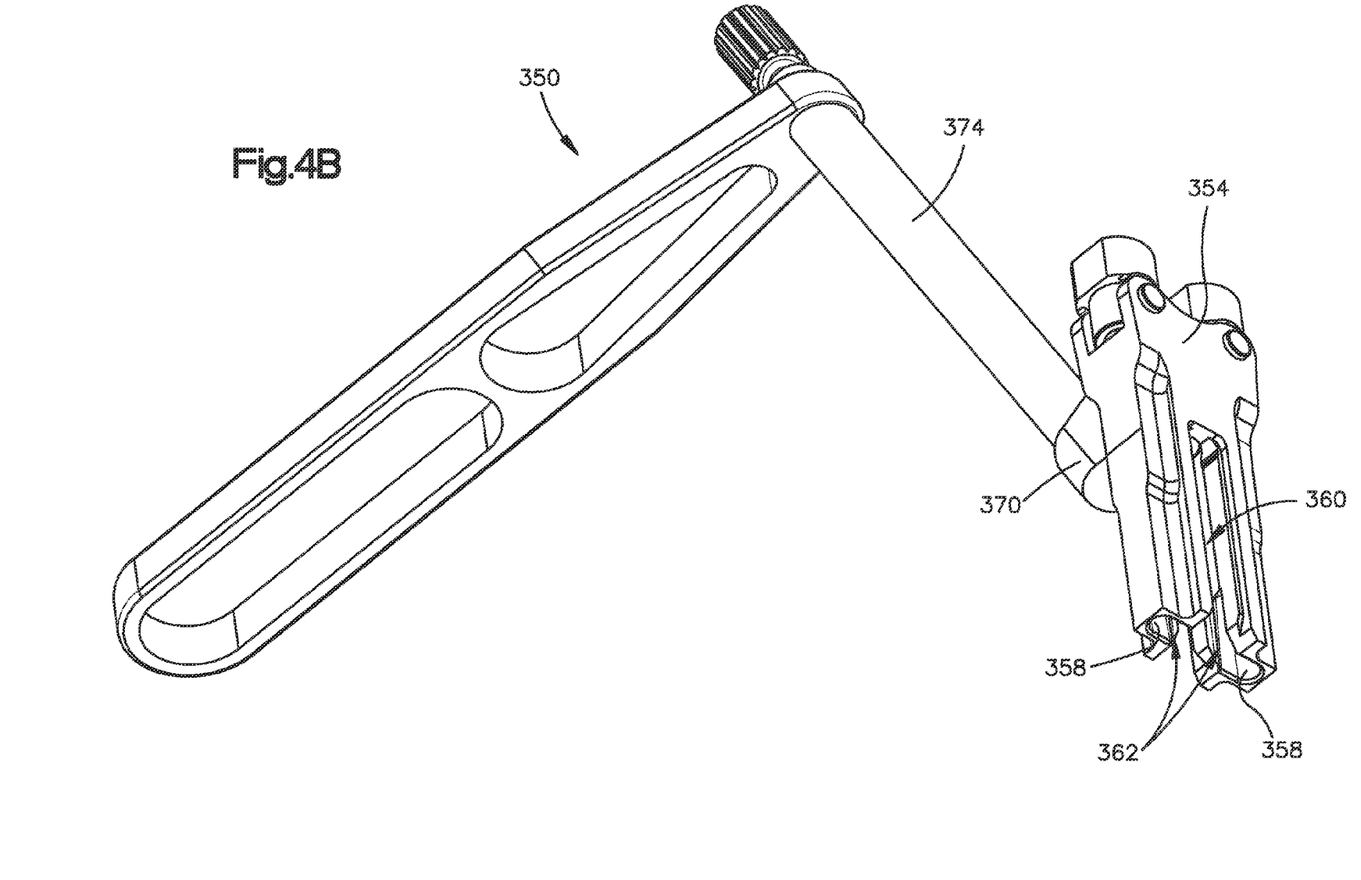
FIG. 4B is a perspective view a milling guide in accordance with one embodiment.
Figure 4C:
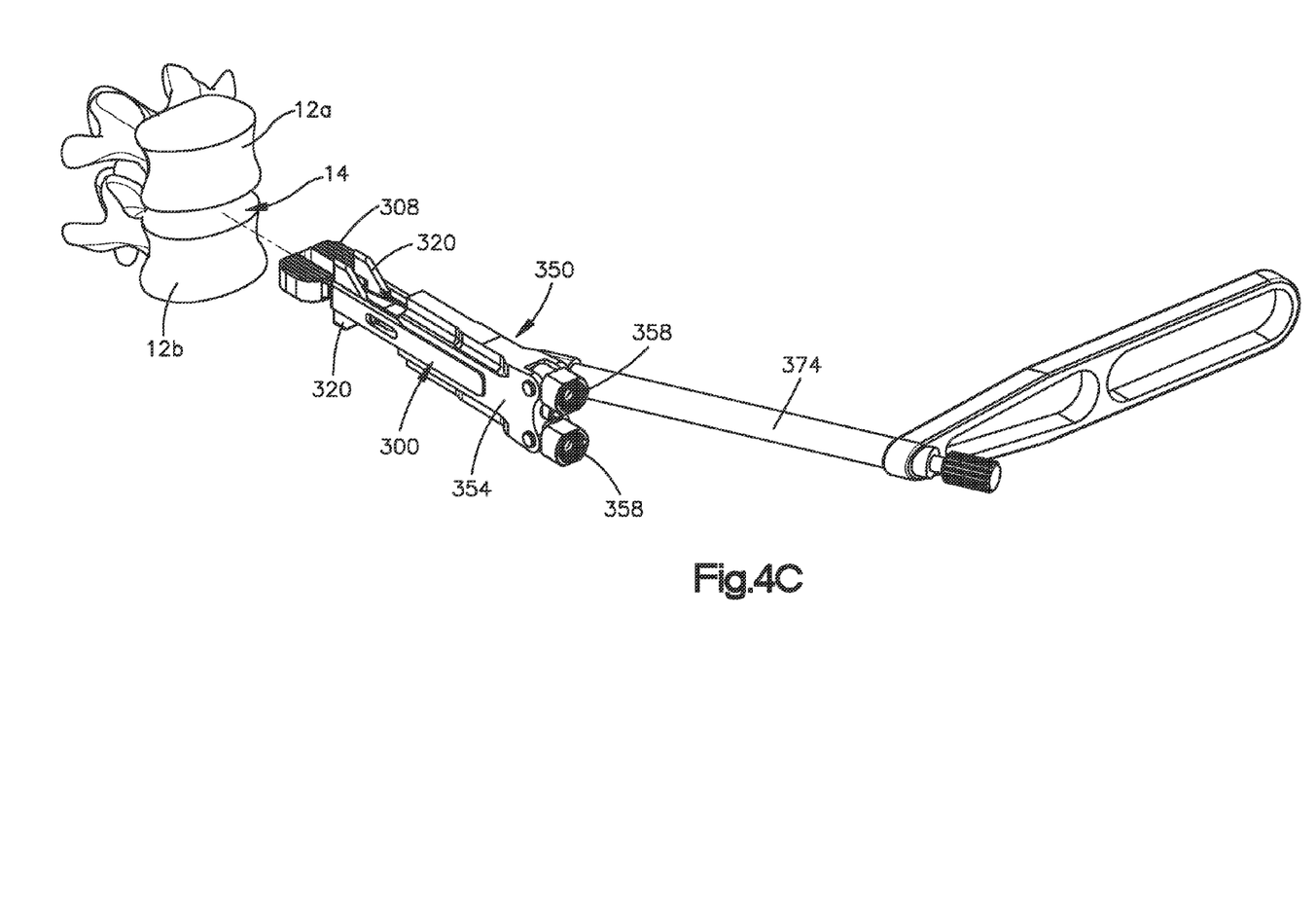
FIG. 4C is a perspective view of the milling guide shown in FIG. 4B mounted onto the trial implant shown in FIG. 4A.

FIGS. 4B and 4C show an example milling guide 350 that may be mounted onto the body 304. As shown, the milling guide 350 includes a body 354 that defines upper and lower chambers 358 that are configured to guide respective reamers. A slot 360 is defined between the chambers 358. In use, the milling guide 350 is mounted onto the body 304 by sliding the milling guide 350 onto the body 304 such that the body 304 is received within the slot 360. Each chamber 358 extends longitudinally through the body 354 and out a distal end of the body 354. As shown, each chamber 358 includes an inner opening 362 at its distal end. The inner openings 362 of the chambers 358 oppose each other. Because of the configuration of the chambers 358, the reamers will be capable of making the inner portions 208, 308 of the first and second keel cuts 200, 204.

The milling guide 350 may also include a coupling mechanism 370 configured to connect the milling guide 350 to a detachable handle 374. The coupling mechanism 370 may be a threaded bore configured to receive a threaded end of the handle 374.

Figure 4D:
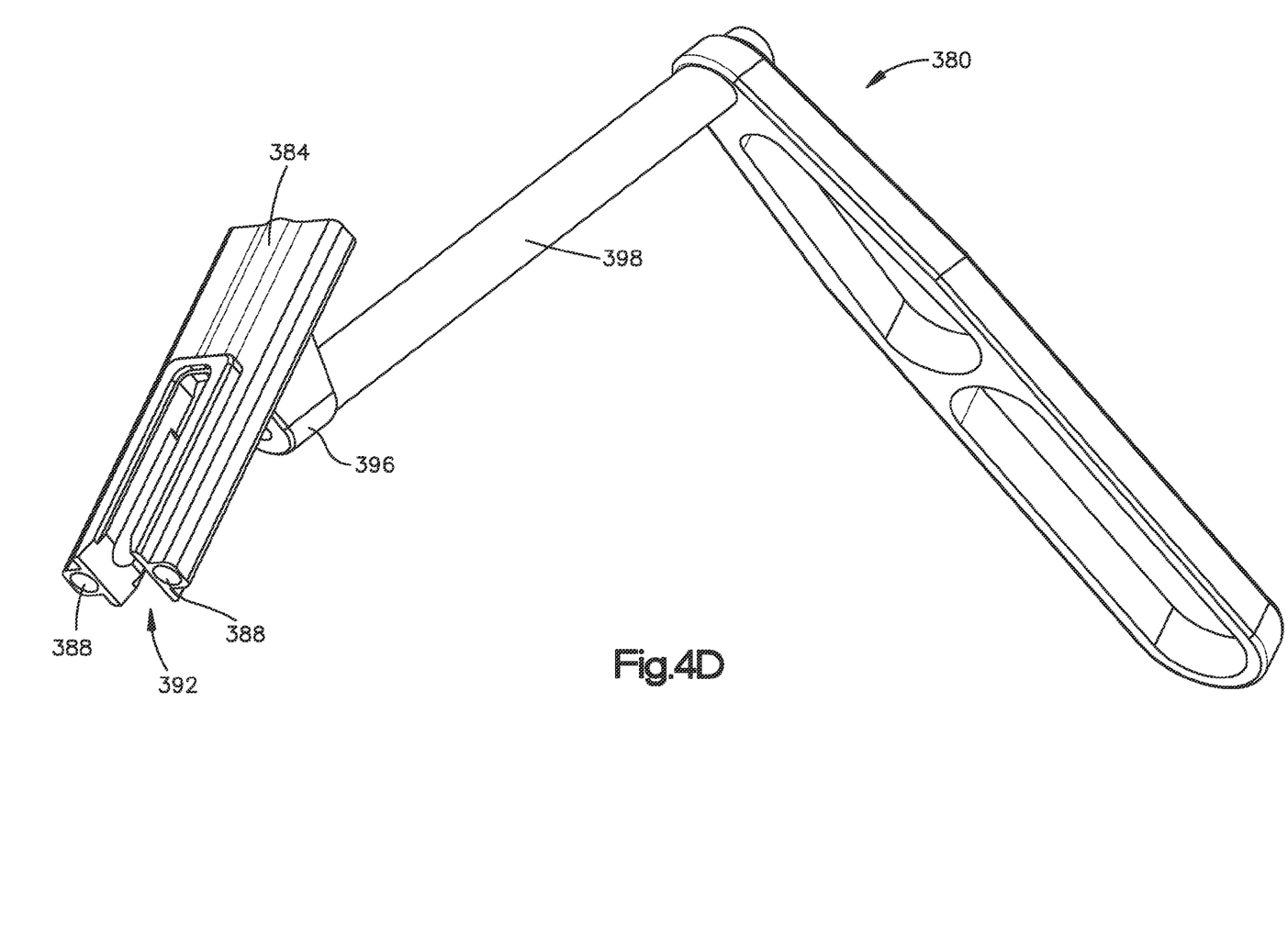
FIG. 4D is a perspective view of a drilling guide in accordance with a first embodiment.
Figure 4E:
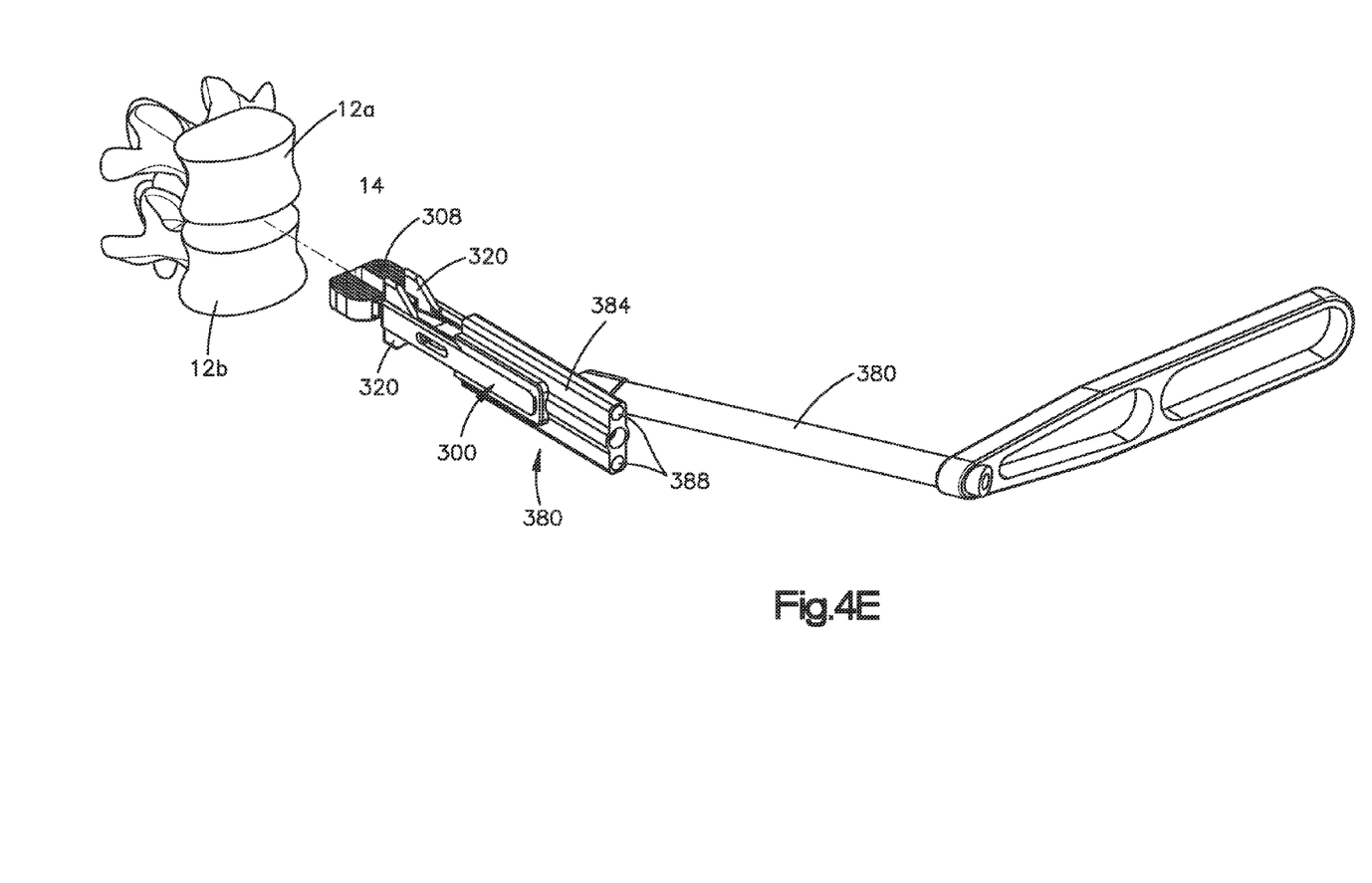
FIG. 4E is a perspective view of the drilling guide shown in FIG. 4D mounted onto the trial implant shown in FIG. 4A.

FIGS. 4D and 4E show an example drilling guide 380 that may be mounted onto the body 304. As shown, the drilling guide 380 includes a body 384 that defines upper and lower chambers 388 that are configured to guide respective drill bits. Like the milling guide 350, the drilling guide 380 includes a slot 392 that is defined between the chambers 388. In use, the drilling guide 380 is mounted onto the body 304 by sliding the drilling guide 380 onto the body 304 such that the body 304 is received within the slot 392. Each chamber 388 extends longitudinally through the body 384 and out a distal end of the body 384. Unlike the chambers 358 of the milling guide 350, the chambers 388 of the drilling guide 380 are cylindrical and preferably not open at their distal ends. Because of the configuration of the chambers 388, the drill bits will be capable of making the outer portions 212, 312 of the first and second keel cuts 200, 204.

The drilling guide 380 may also include a coupling mechanism 396 configured to connect the drilling guide 380 to a detachable handle 398. The coupling mechanism 396 may be a threaded bore configured to receive a threaded end of the handle 398.

In operation, the intervertebral space 14 between the superior and inferior vertebral bodies 12a, 12b is cleared out and the trial head 308 of the trial implant 300 is inserted into the intervertebral space 14 to find the correct height of the implant 20 that will be needed. Once the correct trial head 308 is determined, the trial head 308 is inserted into the intervertebral space 14 until the adjustable stops 312 abut the vertebra. The stops 312 not only secure the trial implant 300 in its right position relative to the vertebral bodies 12a, 12b but they also assure that the trial implant 300 will not slide further back into the spinal canal.

After the trial implant 300 has been correctly positioned, the milling guide 350 is mounted onto the body 304 of the trial implant 300 by sliding the milling guide 350 over the trial body 304. The first portions 208, 308 of the first and second keel cuts 200, 204 may then be formed into the superior and inferior vertebral bodies 12a, 12b by using a reamer or drill with side cutting capabilities. In this regard, the reamer is inserted into the chambers 358 and the surgeon can start cutting along the endplates, and then advance into the vertebral bodies.

Once the first portions 208, 308 of the keel cuts 200, 204 are formed in the superior and inferior vertebral bodies 12a, 12b, the milling guide 350 may be removed and the drilling guide 380 is mounted onto the body 304 of the trial implant 300 by sliding the drilling guide 380 over the trial body 304. The second portions 212, 312 may then be formed in the superior and inferior vertebral bodies 12a, 12b using a drill. In this regard, a drill bit is inserted into the chambers 388 and the outer/second portions 212, 312 may be drilled. It should be understood that the order in which the first and second portions of the keel cuts are formed may be reversed.

Once the intervertebral space 14 is prepared, the anterior end 46 of the implant 20, for instance the engagement member 70, may be coupled to a standard inserter instrument. The implant 20 may then be inserted into the intervertebral space 14 from the anterior side of the space 14 such that the first keel 28 is received by the first keel cut 200 and the second keel 32 is received by the second keel cut 204. As the posterior side 42 of the implant 20 is inserted into the space, the portion of bone disposed between the body facing surfaces 106, 150 of the first and second locking members 84, 114, and the respective outer body surfaces 36, 38 of the insert body 24 is compressed due to the decrease in height of the first and second gaps 160, 190 that is defined therebetween. By compressing the bone, the bone will flow around and conform to the implant 20 and in particular to the first and second keels 28, 32. Following Wolff's Law, bone growth will be enhanced due to the additional pressure.

Once fully inserted within the disc space, the anterior side 46 of the implant 20 is generally flush with the anterior edges of the superior and inferior vertebral bodies 12a, 12b. The flares 92 and 122 of the first and second keels 28, 32 now located completely inside the first and second keel cuts 200, 204 and away from the vertebral edges, prevent anterior migration of the implant 20.

The implant 20 and in particular the keels 28, 32 prevent vertical movement of the superior and inferior vertebral bodies 12a, 12b, relative to each other. This is because the locking members 84 and 114 are wider than their supports 80 and 118, and thereby prevent the vertebral bodies from pulling away from each other. This feature also allows the implant 20 to be inserted and retained within the intervertebral space 14 without the use of additional hardware, such as plates and screws.

Figure 5:
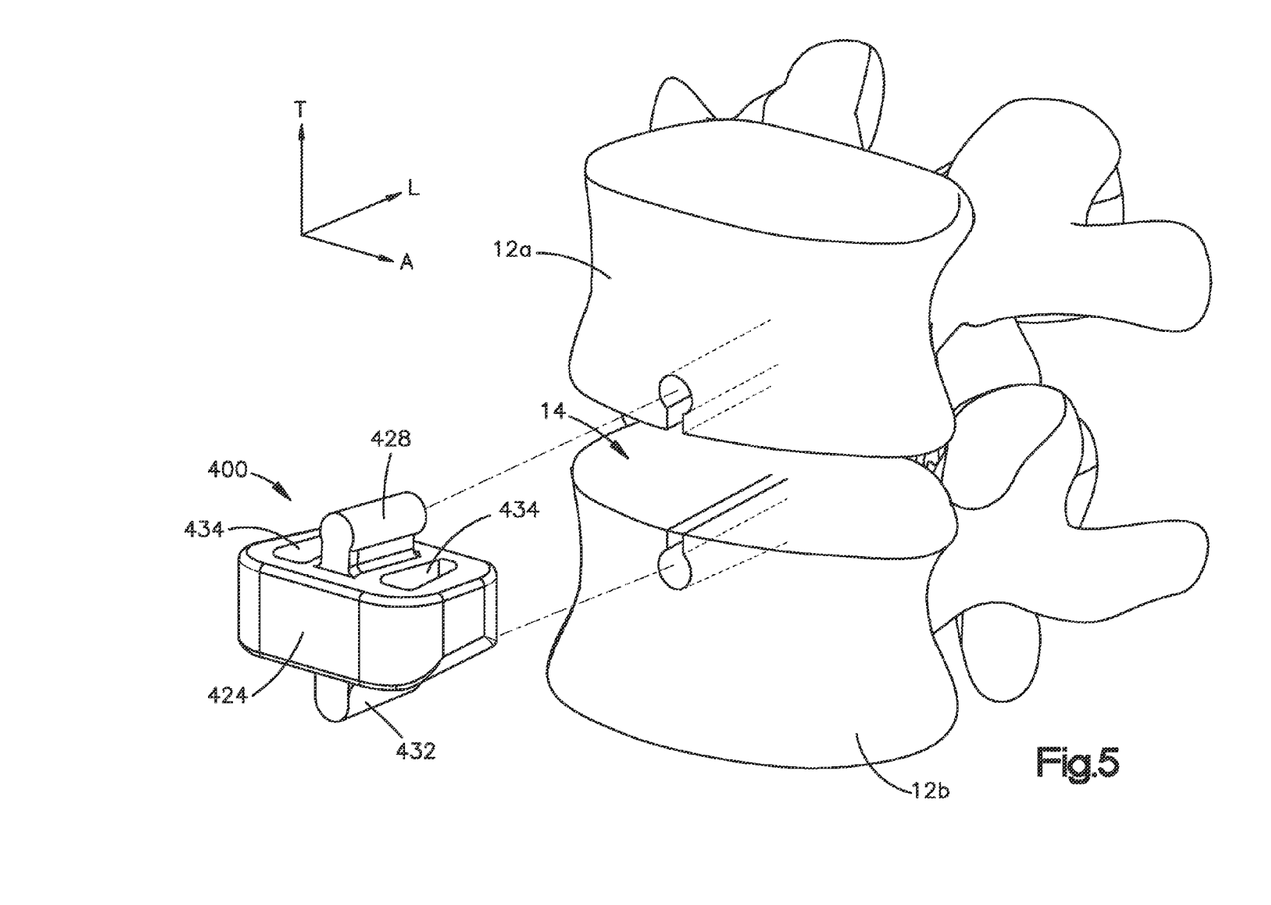
FIG. 5 is a perspective view of an interbody spacer implant in accordance with another embodiment.

Now in reference to FIG. 5, in another embodiment the implant 20 may include vertical bores to promote bone growth. As shown in FIG. 5, an implant 400 includes a body 424, a first keel 428, a second keel 432, and vertical bores 434 that extend vertically through the implant body 424. The bores 426 are elongate in the longitudinal direction and extend on either side of the first and second keels 428, 432. Once the implant 400 is inserted into the intervertebral space, the bores 434 provide a pathway for boney through growth between the superior and inferior vertebral bodies. While the bores 434 are shown as being elongate, it should be understood that the bores 434 may be any shape so long as they extend completely through the implant body 424. Additionally, the bores 434 may be packed with osteogenic or other fusion-assisting materials.

It should be appreciated that the implants 20 and 400 described herein can be configured so as to provide a range of numerous possible geometries and angular relationships. For example, while, the first and second locking members 84, 114 are described as being cylindrical, they may easily be define other shapes such as rectangular blocks. Furthermore, while the first and second keels 28, 32 as well as their respective relationships to the body 24, are described as having similar dimensions and angular relationships, it should be understood that each keel 28, 32 may have different dimensions and angular relationships with respect to the other.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure.

What is claimed:

1. An intervertebral implant configured to be inserted into an intervertebral space along a direction of insertion, the intervertebral space defined by a superior vertebral body and an inferior vertebral body, the intervertebral implant comprising:
a body having first and second opposing outer surfaces each configured to engage one of the superior and inferior vertebral bodies;
a first keel extending out from the first outer surface, the first keel including a first locking member that defines a first body facing surface; and
a second keel extending out from the second outer surface, the second keel including a second locking member that defines a second body facing surface, wherein the first body facing surface diverges from the first outer surface of the body along the direction of insertion, the second body facing surface diverges from the second outer surface of the body along the direction of insertion, and the first and second body facing surfaces converge toward each other along the direction of insertion.

2. The intervertebral implant of claim 1, wherein the first and second keels each define a lateral width that increases with respect to an outward direction along the respective keel such that an outer portion of the respective keel is wider than an inner portion of the respective keel, and wherein the lateral width is substantially transverse to the insertion direction and the outward direction.

3. The intervertebral implant of claim 2, wherein (i) the first keel includes a first support and the first locking member is disposed at an outer end of the first support, (ii) the second keel includes a second support and the second locking member is disposed at an outer end of the second support, and (iii) the first locking member has a lateral width that is greater than the lateral width of the first support, and the second locking member has a lateral width that is greater than the lateral width of the second support.

4. The intervertebral implant of claim 3, wherein the body defines a posterior side and an opposing anterior side, such that at least one of the first and second keels is elongate in substantially the direction of insertion between the posterior and anterior sides.

5. The intervertebral implant of claim 3, wherein an anterior end of the first and second supports defines a flare that curves away from a central axis of the first and second supports in a lateral direction that is substantially transverse to the insertion direction and the outward direction.

6. The intervertebral implant of claim 4, wherein the anterior side of the body defines an engagement member configured to couple the body to an insertion instrument.

7. The intervertebral implant of claim 4, wherein an anterior portion of the first locking member is spaced apart from the first outer surface by a first distance, and a posterior portion of the first locking member is spaced apart from the first outer surface by a second distance that is greater than the first distance.

8. The intervertebral implant of claim 7, wherein an anterior portion of the second locking member is spaced apart from the second outer surface by a first distance, and a posterior portion of the second locking member is spaced apart from the second outer surface by a second distance that is greater than the first distance.

9. The intervertebral implant of claim 4, wherein the first and second outer surfaces converge toward each other along the insertion direction from the anterior side to the posterior side.

10. The intervertebral implant of claim 9, wherein the first and second outer surfaces converge toward each other at a first angle, and the body facing surfaces of the first and second locking members converge toward each other at a second angle that is less than the first angle.

11. The intervertebral implant of claim 1, wherein the body includes a least one bore that extends through the body between the first and second outer surfaces.

12. The intervertebral implant of claim 1, wherein (i) the body defines at least one inferior edge that has a radius $R_I$, and is configured to match a uncinate process of the inferior vertebra.

13. The intervertebral implant of claim 1, wherein the body and the first keel are made from allograft bone.

14. The intervertebral implant of claim 4, wherein the first and second locking members are substantially cylindrical.

15. The intervertebral implant of claim 4, wherein the first and second supports are substantially perpendicular to the first and second outer surfaces of the body.

16. An intervertebral implant configured to be inserted into an intervertebral space along a direction of insertion, the intervertebral space defined by a superior vertebral body and an inferior vertebral body that are opposed in a transverse direction, the intervertebral implant comprising:
   a body having first and second opposing outer surfaces, a posterior side, and an opposing anterior side, wherein the first and second opposing outer surfaces are each configured to engage one of the inferior and superior vertebral bodies;
   a first keel extending out from the first outer surface, the first keel defining a first inner surface that faces the first outer surface of the body; and
   a second keel extending out from the second outer surface, the second keel defining a second inner surface that faces the second outer surface of the body,
   wherein the first and second outer surfaces converge toward each other at a first angle, and the first and second inner surfaces converge toward each other at a second angle that is less than the first angle.

17. The intervertebral implant of claim 16, wherein the first inner surface and the first outer surface define a distance therebetween that increases along the direction of insertion, and the second inner surface and the second outer surface define a distance therebetween that increases along the direction of insertion.

18. The intervertebral implant of claim 17, wherein (i) the first keel includes a first locking member that is elongate between the anterior and posterior sides of the body, and the second keel includes a second locking member that is elongate between the anterior and posterior sides of the body, and (ii) an anterior portion of the first locking member is spaced apart from the first outer surface by a first distance, and a posterior portion of the first locking member is spaced apart from the first outer surface by a second distance that is greater than the first distance.

19. The intervertebral implant of claim 18, wherein an anterior portion of the second locking member is spaced apart from the second outer surface by the first distance, and a posterior portion of the second locking member is spaced apart from the second outer surface by the second distance.

20. The intervertebral implant of claim 16, wherein the first and second outer surfaces converge toward each other along the direction of insertion from the anterior side to the posterior side.

21. The intervertebral implant of claim 20, wherein the first and second locking members define the first and second inner surfaces, respectively.

22. The intervertebral implant of claim 16, wherein the body includes a least one bore that extends from the first and second outer surfaces.

23. The intervertebral implant of claim 16, wherein the body defines at least one inferior edge that has a radius $R_I$, and is configured to match a uncinate process of the inferior vertebra.

24. The intervertebral implant of claim 16, wherein the body, and the first keel are made from allograft bone.

25. The intervertebral implant of claim 18, wherein (i) the first keel includes a first support and the first locking member is disposed at an outer end of the first support, (ii) the second keel includes a second support and the second locking member is disposed at an outer end of the second support, and (iii) the first locking member has a lateral width that is greater than the lateral width of the first support, and the second locking member has a lateral width that is greater than the lateral width of the second support.

* * * * *